United States Patent [19]

Cubbison, Jr.

[11] Patent Number: 5,504,736
[45] Date of Patent: Apr. 2, 1996

[54] NON-INVASIVE LINK MONITOR

[75] Inventor: Richard J. Cubbison, Jr., Westminster, Colo.

[73] Assignee: AT&T Corp., Murray Hill, N.J.

[21] Appl. No.: 946,001

[22] Filed: Sep. 15, 1992

Related U.S. Application Data

[63] Continuation-in-part of Ser. No. 880,842, May 11, 1992, abandoned.

[51] Int. Cl.⁶ .................................................. H04J 1/16
[52] U.S. Cl. ....................... 370/13; 370/24; 375/213; 375/257; 340/825.06; 324/322
[58] Field of Search ............................ 370/13, 24, 29, 370/85.3, 17, 85.13, 27, 28, 13.1, 95.2; 340/825.63, 825.06; 375/10, 36, 121; 324/95

[56] References Cited

U.S. PATENT DOCUMENTS

| | | | |
|---|---|---|---|
| 3,943,283 | 3/1976 | Caragliano et al. | 178/58 R |
| 3,979,699 | 9/1976 | Caragliano et al. | 333/10 |
| 4,467,293 | 8/1984 | Apel | 333/112 |
| 4,493,112 | 1/1985 | Bruene | 455/123 |
| 4,519,066 | 5/1985 | Barrett, Jr. et al. | 370/24 |
| 4,534,038 | 8/1985 | Dodds et al. | 375/121 |
| 4,630,314 | 12/1986 | Smith | 375/58 |
| 4,998,079 | 3/1991 | Theall, Jr. | 333/112 |
| 4,998,240 | 3/1991 | Williams | 370/17 |
| 5,142,690 | 8/1992 | McMullan, Jr. et al. | 370/95.2 |
| 5,179,341 | 1/1993 | Whiteside | 370/13 |
| 5,185,735 | 2/1993 | Ernst | 370/13 |
| 5,197,066 | 3/1993 | Sutterlin | 370/85.3 |
| 5,243,593 | 9/1993 | Timbs | 370/110.1 |
| 5,260,664 | 11/1993 | Graham | 375/10 |
| 5,329,528 | 7/1994 | Akai et al. | 370/13 |
| 5,375,159 | 12/1994 | Williams | 370/13 |
| 5,389,882 | 2/1995 | l'Anson et al. | 370/13 |

OTHER PUBLICATIONS

H. J. Reich et al., *Microwave Theory and Techniques*, D. Van Nostrand Co., Inc., Princeton, N. J. (1953), pp. 364–372, 393.

*The International Dictionary of Physics and Electronics*, 2d. ed., D. Van Nostrand Co., Inc., Princeton, N. J. (1961), pp. 276, 1239.

F. Jay, ed., *IEEE Standard Dictionary of Electrical and Electronics Terms*, 3d. ed., IEEE, Inc., New York, N. Y. (1984), p. 258.

L. J. Giacoletto, ed., *Electronics Designers' Handbook*, 2d ed., McGraw–Hill Book Co., New York, N. Y. (1977), pp. 8–63 to 8–65.

Sybil P. Parker, ed., *Encyclopedia of Electronics and Computers*, 2d ed., McGraw–Hill Book Co., New York, N.Y. (1988), pp. 269–270.

Martin H. Weik, *Communications Standard Dictionary*, Van Nostrand Reinhold Co., Inc., New York, N. Y. (1983), pp. 251–252.

(List continued on next page.)

*Primary Examiner*—Douglas W. Olms
*Assistant Examiner*—Shick Hom
*Attorney, Agent, or Firm*—David Volejnicek

[57] ABSTRACT

A non-invasive directional coupler (51) comprising a voltage probe (300) and a current probe (301) is used to detect and separate from each other digital pulses (quats) being transmitted in opposite directions on a digital ISDN subscriber loop 200 (U-interface 15). The voltage probe measures the sum of digital pulse voltage of the conductors (201, 202) of the loop while the current probe measures the difference of digital pulse currents of in the conductors. An equalizer (304) converts the difference of the currents into the difference of the corresponding voltages. The sum and difference voltage measurements are then added (305) and subtracted (306) respectively to obtain voltages for digital pulses propagating in each direction. The voltages are provided to a decoder (52) such as a protocol analyzer for processing to interpret the traffic being sent in each direction on the loop.

33 Claims, 6 Drawing Sheets

OTHER PUBLICATIONS

John Markus, *Electronics Dictionary,* 4th ed., McGraw–Hill Book Co., New York, N.Y. (1978), p. 176.

Rudolf F. Graf, *Modern Dictionary of Electronics,* 6th ed., Howard W. Sams & Co., Inc. Indianapolis, IN (1984), p. 271.

Am 79C02/3(A) DSLAC™ Device, product description, Advanced Micro Devices (Jul. 1991).

Chu et al. 'Analysis and Development of a Signal Injection Technique Using Transmission Lines Enbedded at Phased Array Aperture' IEEE Transactions on Antennas and Propagation vol. 41, No. 10 (1993): 1464–69

# 5,504,736

NON-INVASIVE LINK MONITOR

This application is continuation-in-part of application Ser. No. 07/880,842, filed on May 11, 1992, now abandoned.

TECHNICAL FIELD

This invention relates generally to transmission systems, and relates particularly to line testing and monitoring arrangements for telecommunications transmission systems.

BACKGROUND OF THE INVENTION

The need often arises for monitoring transmissions on a communications link, for example in order to determine whether the link and its associated transmission equipment are working properly and to diagnose the problem if they are working improperly. Various arrangements exist in the prior art for enabling a craftsperson to do so in certain environments. For example, the twisted-wire pair subscriber loop of a conventional analog baseband telephony system could be directly monitored by a service technician simply by connecting a handset across the tip and ring leads of the loop. Higher-rate analog simplex transmission systems could theoretically be monitored to some extent visually via an oscilloscope connected across the leads of the transmission line, and simplex or duplex non-time-division-multiplexed analog systems could be monitored by a service technician aurally using demodulators analogous to radio receivers.

Digital transmission systems present challenges not encountered in the analog domain, however. Not only are communications encoded in digital form which must be decoded in order to make the communications recognizable to the craftsperson, but they also typically employ protocols whose informational units are transmitted interspersed with the communications. In a full-duplex system where transmissions are proceeding in both directions at the same time, this produces a jumble of electrical signals on the transmission link that is not readily decipherable by any known means of external (i.e., non-invasive) observation. An example of such a digital transmission system is the digital subscriber loop of modem ISDN telephony systems.

The prior art has provided service technicians with an ability to monitor communications in such duplex digital transmission systems through the use of protocol analyzers. The use of a protocol analyzer requires the technician either to connect the analyzer to the communication link at a termination, i.e., an end thereof, or to cut the communication link and connect the protocol analyzer in series with the two portions of the link. In the first instance, the protocol analyzer substitutes for the transmitter/receiver at one end of the link and turns the link into a simplex communication medium. In the second instance, the protocol analyzer receives the oppositely-directed simultaneous (duplex) transmissions separately, each on a different one of the two portions of the link. In either instance, the protocol analyzer may decode received communications in the same manner as would a conventional piece of equipment on the receiving end of the link.

The problems with these approaches are self evident. In the first instance, they limit the physical points at which the link may be monitored to only the two points of termination, e.g., at a customer's premises and at a telephony central office. This is impractical for many applications, e.g. field link-servicing and repair. In the second instance, the transmission link must be physically interrupted—cut—to allow connection of the monitoring equipment thereto. This causes both physical damage to the link and interruption of any communications being transmitted thereon. The physical damage is difficult and expensive to repair in a fault-free manner, i.e., in such a way that it will not be likely to cause problems in the future, and the interruption of communications degrades communication capabilities and makes in-service testing of communication links impossible or at least undesirable.

Hence, what is required is a non-invasive technique—one that does not cause physical interruptions and electrical (service) disruptions—for monitoring transmission links, such as full duplex digital ISDN telephony loops, substantially at any point thereof.

SUMMARY OF THE INVENTION

This invention is directed to solving these and other disadvantages of the prior art. Generally according to the invention, a directional coupler is non-invasively coupled to a transmission link, such as a digital subscriber loop, to detect traffic (e.g. digital signals) being transmitted thereon and to separate traffic being transmitted in opposite directions. The coupler illustratively comprises a voltage detector for measuring signal voltage on the link, a current detector for measuring signal current on the link, and circuitry to derive from the measured signal current and signal voltage representations of the traffic flowing in each direction. The representations of the separated traffic are then advantageously provided to a processor, such as a protocol analyzer, for interpretation to determine the meaning of the traffic. In this manner, the traffic being transmitted on the link in one or both directions may be effectively monitored.

According to an illustrative embodiment of the invention, the non-invasive directional coupler comprises the following four elements. First, means for measuring a sum of voltages of signals on a plurality of conductors of the link, such as a voltage probe having two leads each in conductive contact with a different one of a pair of conductors of the link for sensing signal voltages on the conductors, and a differential voltage probe interface for generating a first signal representing the sum of the sensed signal voltages. Second, means for measuring a difference of the currents of signals of the plurality of conductors of the link, such as a current probe not in conductive (e.i. metallic) contact with, and electromagnetically coupled to, the pair of conductors for sensing the signal currents of the conductors, and a current probe interface for generating a second signal representing the difference of the sensed signals currents. Third, means for converting the measurement of one of the currents and the voltages into a corresponding measurement of the other of the currents and the voltages, such as an equalizer for converting the second signal which represents the of the sensed signal currents into a third signal representing the difference of the signal voltages of the pair of conductors. And fourth, means for generating signals representing one (or for generating separate signals each representing a different one) of a sum and a difference of the voltage or current measurement that has not been converted and the corresponding voltage or current measurement of the current or voltage measurement that has been converted, such as one (or both) of a sum circuit and a difference circuit each for combining the first signal with the third signal and generating a signal representing the combination. The signal generated by the sum circuit represents traffic being transmitted in one direction, while the signal generated by the difference circuit represents traffic being transmitted in the other direction.

The coupler is non-invasive, both physically in that it does not require an interruption of the transmission line in order to couple thereto, and electrically in that it does not substantially affect the electrical characteristics (e.g., transmission characteristics, voltages, currents) of the transmission link and does not interfere with the transmissions on the link. The coupler may be connected to the transmission link at any point. In the illustrative implementation, the coupler is uncomplicated, compact, and inexpensive. It is effective in separating full-duplex traffic, and provides representations of the separated traffic in a form suitable for input to conventional protocol analyzers.

These and other advantages and features of the invention will become apparent from the following description of an illustrative embodiment of the invention taken together with the drawing.

DETAILED DESCRIPTION

Figure 1:
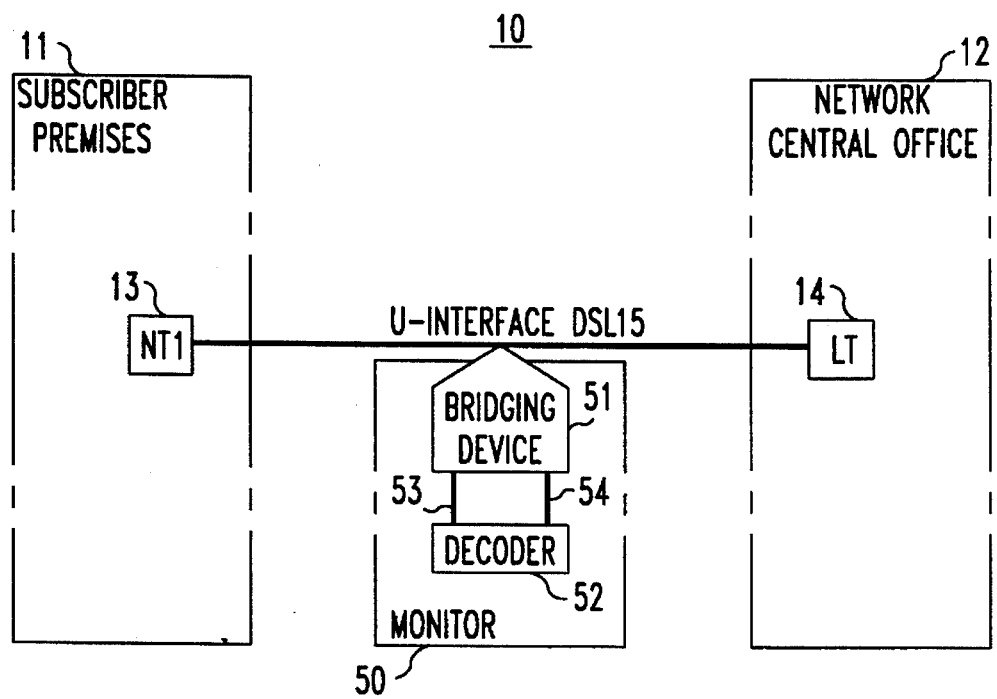
FIG. 1 is a block diagram of a digital transmission system making use of an illustrative embodiment of the invention.

FIG. 1 shows an illustrative digital ISDN communications transmission system 10 that makes advantageous use of the present invention. The shown system 10 interconnects subscriber premises 11 with a central office 12 of a communications network such as the public telephone network. The transmission medium of system 10 is the digital subscriber line or loop (DSL) 15 which, according to CCITT ISDN standards, terminates at a line termination (LT) 14 at network central office 12 and terminates in a network termination 1 (NT1) 13 at subscriber premises 11. According to the parlance of the CCITT ISDN standards, DSL 15 is known as the U interface.

The CCITT ISDN standards define the U interface at layer 2 of the ISO OSI hierarchy to consist of two 64 kbps clear B channels plus one 16 kbps packetized signaling D channel—known as the "2B+D" or "basic rate" interface. But the CCITT ISDN standards do not define the characteristics of the U interface at layer 1 of the OSI hierarchy. The definition of these characteristics is left to individual countries.

In the U.S.A., layer 1 of the U interface is defined in ANSI North American Standard T1.601-1991. According to the ANSI standard, transmission over DSL 15 is full duplex and proceeds in the form of binary data having the alphabet B=(0, 1) at a bit rate of 160 kbps. The modulation technique adopted by the ANSI standard for use over a primary-rate DSL 15 is called 2B 1Q line coding. According to this coding technique, successive pairs of binary data B are one-to-one mapped onto successive units of quaternary symbols with alphabet Q=(−3, −1, +1, +3) and transmitted as a corresponding voltage level at half the rate of the binary sequence. Therefore, an incoming binary stream B with bit rate of 160 kbps is converted into a quaternary stream Q with symbol (baud) rate of 80 kbps and then transmitted from NT1 13 or LT 14 over DSL 15. The quaternary symbols or pulses are referred to as "quats".

As shown in FIG. 1, to enable the monitoring of communications on DSL 15, there is employed a monitor 50. Monitor 50 comprises a bridging device 51 and a decoder 52. Bridging device 51 connects monitor 50 to DSL 15, detects the coded full-duplex, merged, transmissions stream on DSL 15, and separates the transmissions into the two components of transmission each one of which is propagating in the opposite direction. Bridging device 51 then provides the separated digital components of the transmission stream over separate links 53 and 54 to decoder 52 for decoding. Illustratively, decoder 52 is a conventional device, such as a protocol analyzer.

Figure 2:
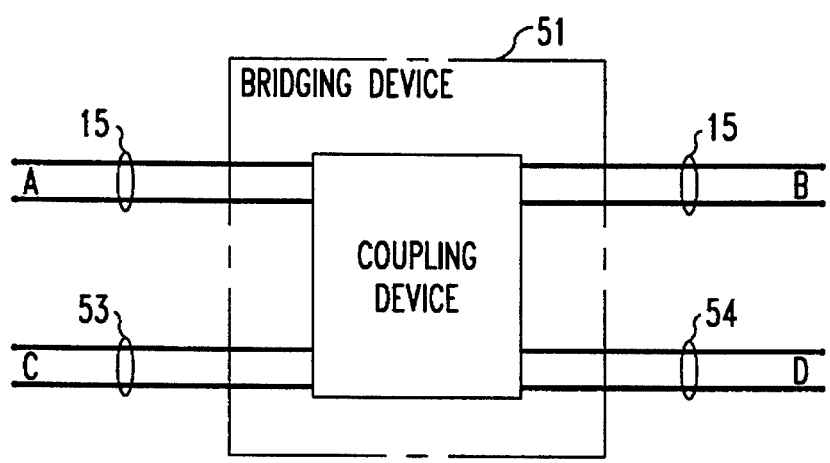
FIG. 2 is a block diagram of the theoretical concept of the bridging device of the monitor of the system of FIG. 1.

According to the invention, bridging device 51 is a form of a directional coupler (also sometimes referred to as a bi-directional coupler). The concept of a directional coupler is illustrated in FIG. 2 and is defined as follows: "A directional coupler is a junction between four pairs of terminals, as shown in [FIG.], having such characteristics that there is free transfer of power, without reflection between terminals A and B and no transfer of power between terminals A and C or between terminals B and D. Thus an indication of power at point D indicates that power is flowing from A to B while an indication at C indicates power flow from B to A." *The International Dictionary of Physics and Electronics* 276, D. Van Nostrand Co., Inc. (2d ed. 1961); also see H. J. Reich et al., *Microwave Theory and Techniques* 364–372, D. Van Nostrand Co., Inc. (1953).

Figure 3:
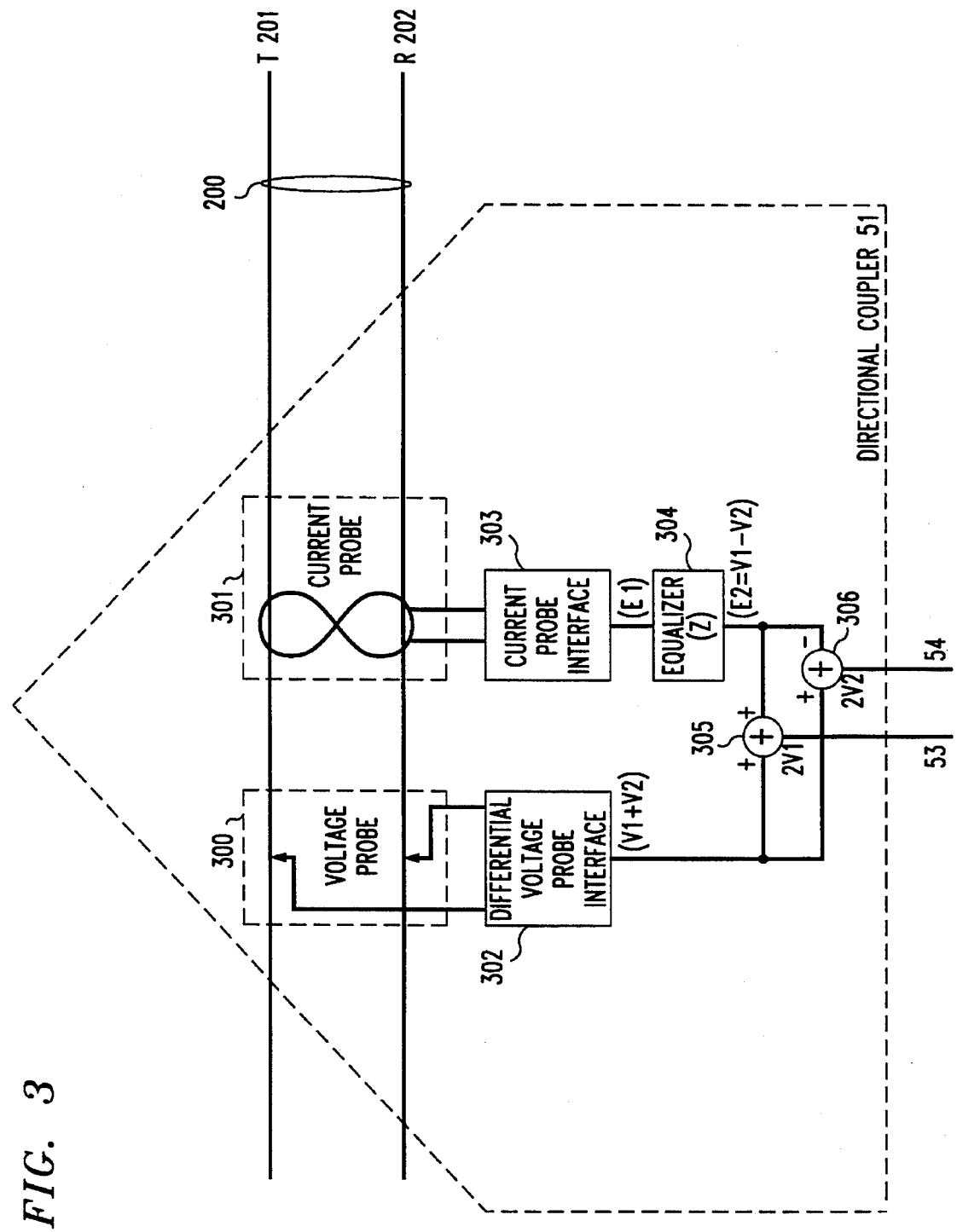
FIG. 3 is a block diagram of a first illustrative implementation of the bridging device of the monitor of the system of FIG. 1.
Figure 4:
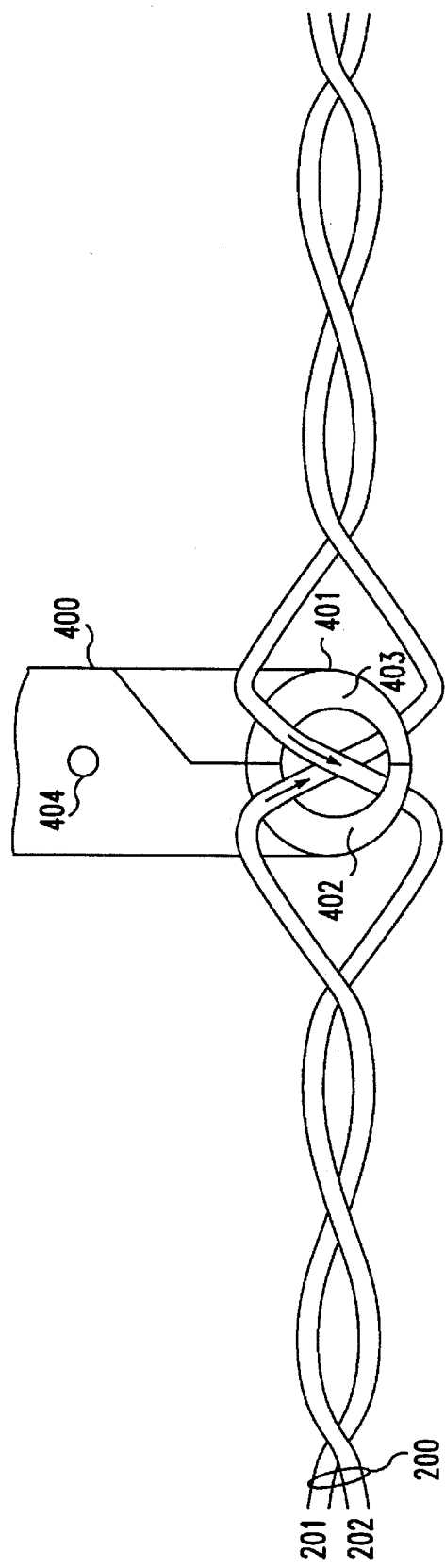
FIG. 4 is an illustration of the physical coupling of the current probe of the bridging device to the twisted wire pair in FIG. 3.

The physical medium that commonly, and almost exclusively, implements DSL 15 in the U.S.A. is the conventional telephony twisted-wire pair 200 consisting of a tip (T) lead 201 and a ring (R) lead 202 (see FIGS. 3 and 4). A novel implementation of a directional coupler for use with such a DSL 15 is shown in FIG. 3. It uses a conventional voltage probe 300 and a conventional current probe 301 to capture the merged transmission stream from DSL 15. Voltage probe 300 is illustratively a pair of leads terminating at clips—such as are commonly used with an oscilloscope—which make conductive contact across leads 201 and 202. Voltage probe 300 is coupled to the other circuitry of directional coupler 51 via a conventional differential voltage probe interface 302, such as a Tektronix P6046 differential voltage probe. Interface 302 provides a high-impedance balanced differential input for purposes of common-mode signal rejection and minimization of tip-ring line loading and interference.

Current probe 301 is illustratively the P6021 current probe from Tektronix, Inc., which clips around leads 201 and 202. Current probe 301 accesses the current in leads 201 and 202 without being inserted in series with the metallic path or making conductive contact with it. Rather, current probe 301 makes a free-space electromagnetic-field connection with leads 201 and 202. Current probe 301 is coupled to the other circuitry of directional coupler 51 via a conventional current probe interface 303, such as a Tektronix P6021 AC current probe. Interface 303 provides gain and equalizes the magnetic response characteristics of core 401 and turns the response into a voltage E1.

As shown in FIG. 4, the head 400 of current probe 301 carries a magnetic core 401 made up of two sections 402 and 403 that are articulated (e.g., around a point 404) with respect to each other, or are otherwise openable. The two articulated sections of core 401 simply open to admit both insulated leads 201 and 202, and when closed around leads 201 and 202, measure the AC component of their magnetic fields.

The currents in the tip and ring leads 201 and 202 at a single point along twisted-pair 200 have the same instantaneous magnitude but they have opposite polarities. They are 180 degrees out of phase with respect to each other, just as the voltage from tip to ground carries an opposite polarity to that from ring to ground. However, the noise currents which are coupled equally into the tip and ring together have the same magnitude and polarity. Hence, a special technique is required when using the current probe, for the elimination of unwanted longitudinal currents.

The special technique involves untwisting a short portion of tip lead 201 from ring lead 202 and routing them both through probe head 400 in opposite directions, as shown in FIG. 4. The longitudinal noise currents then pass through core 401 in opposite directions and hence cancel out, while the composite quat currents pass through with the same polarity and therefore sum.

Probes 300 and 301 capture the merged quats flowing along twisted-wire pair 200 as analog voltage and current measurements, respectively. Consequently, there is the problem of separating the individual quats from these composite, merged, measurements. To separate merged quats captured as analog voltage measurements, it is necessary that the separate quats be distinct from one another either in pulse shape or phase.

Alternative techniques to the just-described composite voltage and current measurements do exist, but are not favored. Amplitude is an obvious feature of pulse shape which can be used to separate quats captured as single point voltage measurements. Table I shows how two quats having different pulse voltages sum arithmetically in the voltage measurement of DSL 15 to create a composite pulse voltage. As shown, each possible composite quat measurement correlates uniquely with a separate quat combination. This makes it possible to uniquely separate two quats from the resulting voltage composite as long as they have a sufficient difference in pulse amplitude. This difference is due to the different amount of attenuation received by each quat as it reaches bridging device 51 from a different direction and distance.

TABLE I

| QUAT | POSSIBLE VOLTAGE LEVELS |
|---|---|
| QUAT 1 | +2.5, +.83, −.83, −2.5 |
| QUAT 2 | +1.5, +.50, −.50, −1.5 |

| QUAT COMBINATION | | |
|---|---|---|
| QUAT 1 | QUAT 2 | COMPOSITE QUAT VOLTAGE LEVEL |
| +2.50 | +1.50 | +4.00 |
| +2.50 | +0.50 | +3.00 |
| +2.50 | −0.50 | +2.00 |
| +2.50 | −1.50 | +1.00 |
| +0.83 | +1.50 | +2.33 |
| +0.83 | +0.50 | +1.33 |
| +0.83 | −0.50 | +0.33 |
| +0.83 | −1.50 | −0.67 |
| −0.83 | +1.50 | +0.67 |
| −0.83 | +0.50 | −0.33 |
| −0.83 | −0.50 | −1.33 |

TABLE I-continued

| −0.83 | −1.50 | −2.33 |
|---|---|---|
| −2.50 | +1.50 | −1.00 |
| −2.50 | +0.50 | −2.00 |
| −2.50 | −0.50 | −3.00 |
| −2.50 | −1.50 | −4.00 |

TABLE II

| QUAT | POSSIBLE VOLTAGE LEVELS |
|---|---|
| QUAT 1 | +2.5, +.83, −.83, −2.5 |
| QUAT 2 | +2.5, +.83, −.83, −2.5 |

| QUAT COMBINATION | | |
|---|---|---|
| QUAT 1 | QUAT 2 | COMPOSITE QUAT VOLTAGE LEVEL |
| +2.50 | +2.50 | +5.00 |
| +2.50 | +0.83 | +3.33 |
| +2.50 | −0.83 | +1.67 |
| +2.50 | −2.50 | 0.00 |
| +0.83 | +2.50 | +3.33 |
| +0.83 | +0.83 | −1.67 |
| +0.83 | −0.83 | 0.00 |
| +0.83 | −2.50 | −1.67 |
| −0.83 | +2.50 | +1.67 |
| −0.83 | +0.83 | 0.00 |
| −0.83 | −0.83 | −1.67 |
| −0.83 | −2.50 | −3.33 |
| −2.50 | +2.50 | 0.00 |
| −2.50 | +0.83 | −1.67 |
| −2.50 | −0.83 | −3.33 |
| −2.50 | −2.50 | −5.00 |

If the distances are similar, the attenuations will be similar, and so with the pulse amplitudes. This condition is illustrated in Table II, where it is shown that composite quat voltage measurements no longer uniquely represent just one combination of quats. This makes it necessary to choose between two possible quat combinations for some of the composite quat voltage measurements. If this becomes necessary, discrimination at a higher level can be invoked based on quats already collected and probabilities using an understanding of the ISDN protocol. Unfortunately, even this elaborate processing will not guarantee errorless quat separation for the case where the quat pulse amplitudes are too close together.

Dual-point voltage measurements of DSL 15 offer an opportunity to provide two equations in two unknowns. The two unknowns are the two quat pulse voltages which are added in DSL 15 to create the composite voltage measurement. The two equations come from the two voltage measurements which are made at different points along DSL 15. If the quats had the same attenuation and delay at each measurement point, the two voltage measurements would be identical. If the points of measurement are sufficiently separated from one another, the colliding quats will have different levels at each point of measurement, due to propagation losses and delays. Then, when the colliding quats combine at each point, they combine differently at the two points. One then has two equations in two unknowns. This, however, would not be true if the two points were close together. And, in practice, the separation of the two points of measurement must be too great in order to produce an appreciable difference that can practicably be measured. Hence, this approach is not favored.

Figure 5:
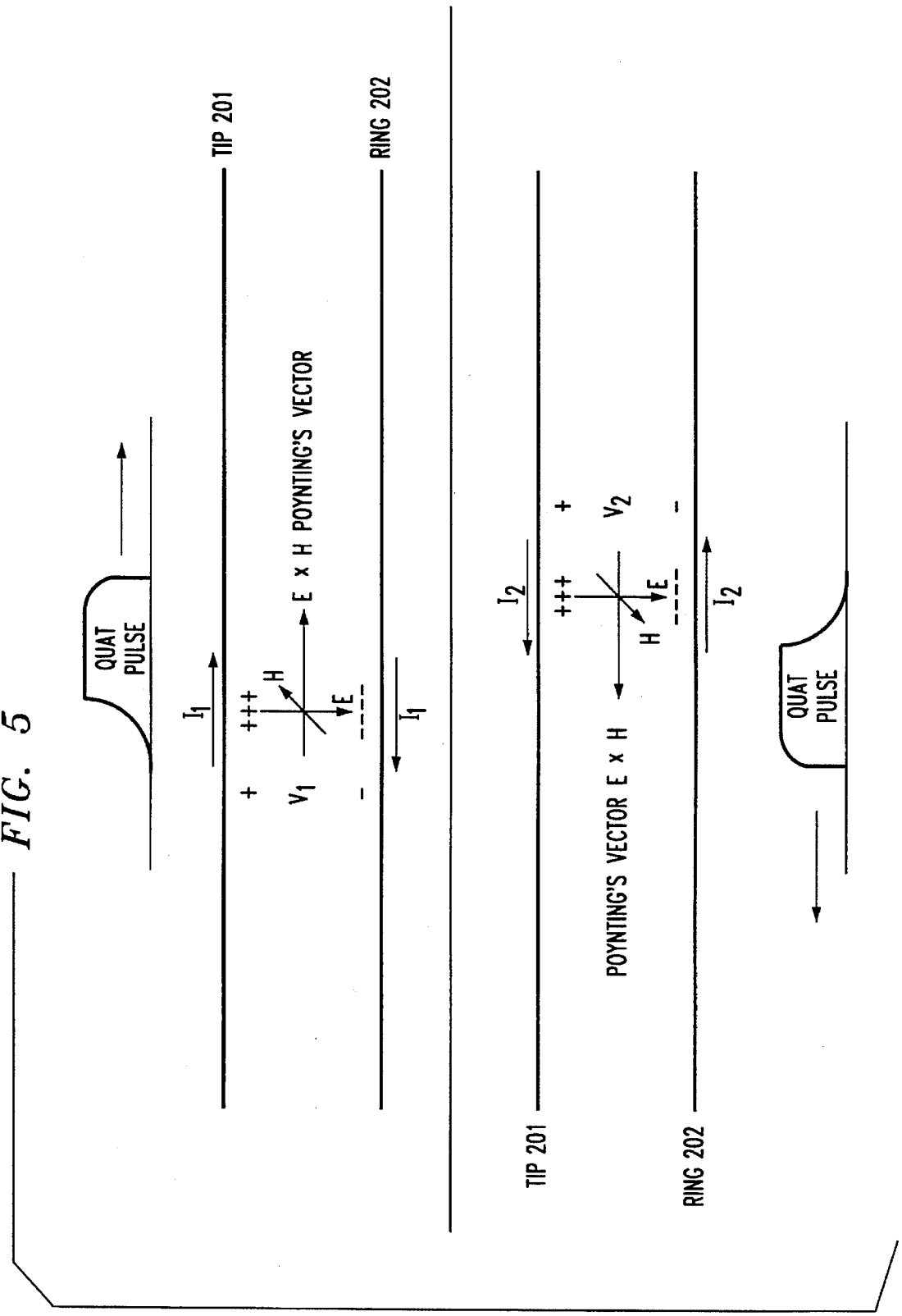
FIG. 5 is an illustration of the physics involved in the measurement performed by the bridging device of FIG. 3.

Favored instead is the approach shown in FIG. 3, which relies upon the single-point measurement of voltage and of current in order to create two equations in two unknowns. Due to the opposite directions of propagation taken by the quats to be separated, their voltages do not add into a composite voltage in the same way that their currents add to form a composite current. If it happens that the two quats have the same voltage polarity at some instant, their currents have opposite polarities because of their oppositely directed propagations. If the quats have opposite voltage polarities, they then share the same current polarity, and so on, through all other phase variations. This is shown in FIG. 5, which is a representation of a single transmission link showing separately the voltages and currents of quats propagating in opposite directions. When these voltages and currents are combined in the one link, the currents sum algebraically, as do the voltages.

The abovementioned combinations of voltages and currents can be seen more clearly in the following two equations:

$$V = V1 + V2$$

$$I = I1 - I2$$

where:
V is the composite quat voltage across tip and ring,
I is the composite quat current through tip and ring,
V1 is the voltage of a quat propagating from left to right,
V2 is the voltage of a quat propagating from right to left,
I1 is the current of a quat propagating from left to right, and
I2 is the current of a quat propagating from right to left.

The V1 and V2 voltages are related to their respective I1 and I2 currents by the same impedance in most circumstances at the point of measurement even though the pulses are propagating in opposite directions. In most other circumstances the impedances can generally be treated as being the same. This impedance is due to the combined effects of the DSL 15 characteristic impedance and the end point interfaces. The magnitude of that impedance varies around an average near 135 ohms over the band of interest. While assuming this to be a constant value with no phase angle is simplistic, this value serves to demonstrate how the above two equations are solved for V1 and V2.

Assuming Z represents the combined impedances of the end point interfaces with DSL 15, then the voltages and currents are related by:

$$V1 = I1 \cdot Z$$

$$V2 = I2 \cdot Z$$

With these and the two previous equations, V1 and V2 are algebraically resolved into their values below:

$$V1 = (V + I \cdot Z)/2$$

$$V2 = (V - I \cdot Z)/2$$

The computations which are described above in conjunction with FIG. 5 are effected in directional coupler 51 of FIG. 3 in the following manner. The voltage E1 output by current probe interface 303 is input to an equalizer 304. Many simpler alternatives to an equalizer will occur to a person skilled in the art, such as a fixed-impedance network or an adaptive balnet (hybrid balancing network). Equalizer 304 represents the variable Z of the equations given above. It has a magnitude and a phase of equalization that performs a transfer function that converts the difference of currents I1 and I2 that is used by current probe 301 into the difference of voltages V1 and V2 that is needed to solve the equations given above. Equalizer 304 takes the voltage E1 which corresponds to I1–I2 and converts it into another voltage E2 which corresponds to V1–V2.

Illustratively, as an approximation, the value of Z may be taken to be 135 ohms, with no phase angle at any frequency of interest. More precisely, however, the value of Z is represented by the Laplace transfer function $$T(s) = \frac{E_1}{E_2} = K \frac{S^N + W_{Z1} S^{(N-1)} + \ldots W_{ZN}^N}{S^N + W_{P1} S^{(N-1)} + \ldots W_{PN}^N}$$

where K is the gain constant,
S is the Laplace transform variable,
$W_{Z1} \ldots W_{ZN}$ are the numerator coefficients,
$W_{P1} \ldots W_{PN}$ are the denominator coefficients,
W is the radian frequency,
Z is a subscript representing the influence of transmission zeros on the numerator coefficients,
P is a subscript representing the influence of transmission poles on the denominator coefficients; and
N is the order of the function.

Figure 6:
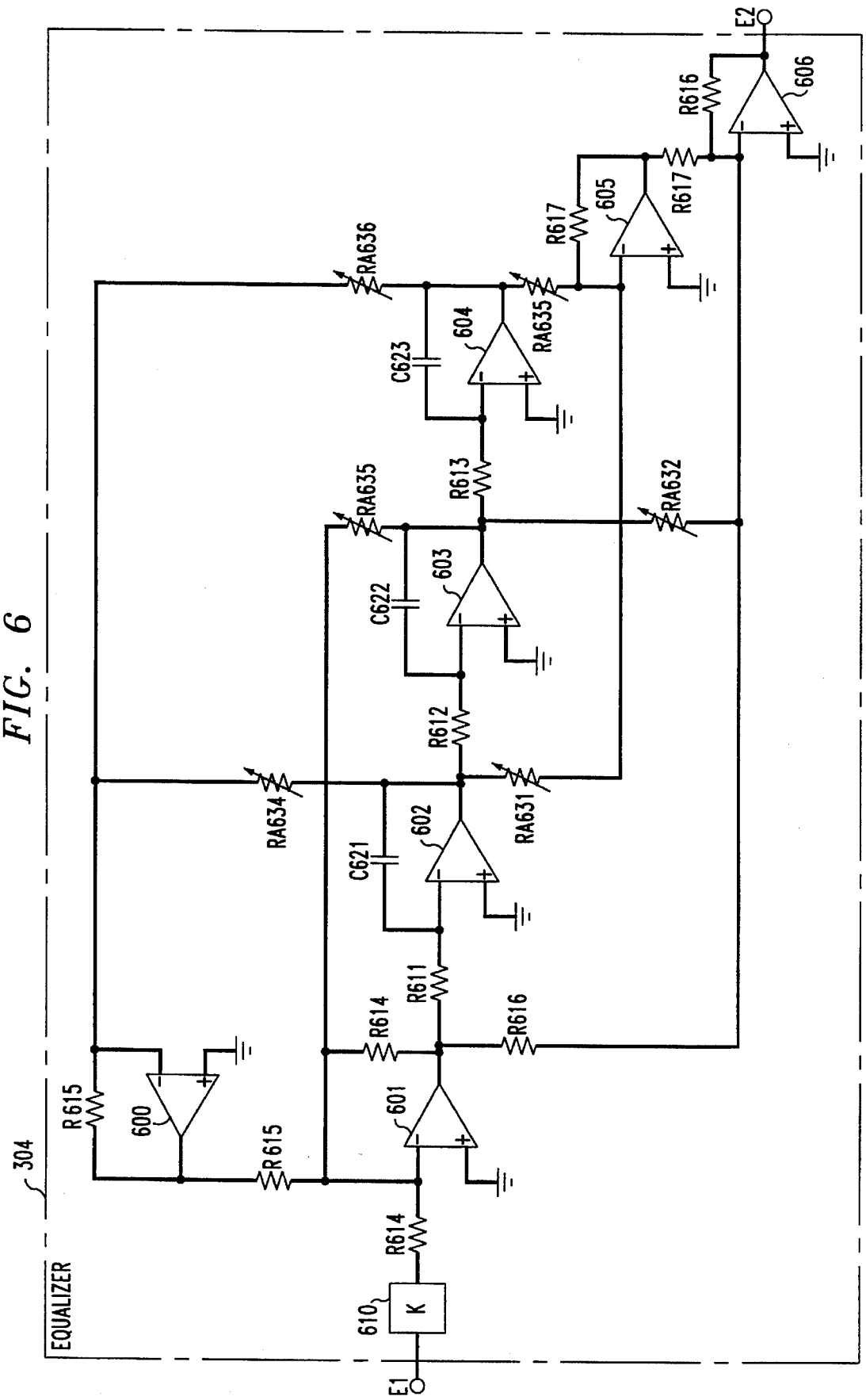
FIG. 6 is a circuit diagram of an illustrative implementation of the equalizer of the bridging device of FIG. 3.

The formulation and solution of such transfer functions are well within the skill of the arts of 2-to-4 wire wideband hybrid design and wideband echo canceller design. Illustratively, FIG. 6 shows an implementation of equalizer 304 for a value of N=3. In FIG. 6, element 610 is an amplifier having an amplification factor of K, elements 600–606 are operational amplifiers, elements C621–C623 are capacitors, elements R611–R617 are resistors, and elements RA631–RA636 are potentiometers. For the circuit of FIG. 6, the transfer function given above reduces to $$T(s) = \frac{S^3 + \frac{R616}{RA631} W_1 S^2 + \frac{R616}{RA632} W_1 W_2 S + \frac{R616}{RA633} W_1 W_2 W_3}{S^3 + \frac{R614}{RA634} W_1 S^2 + \frac{R614}{RA635} W_1 W_2 S + \frac{R614}{RA636} W_1 W_2 W_3}$$

where $$W_1 = \frac{1}{R611 \cdot C621},$$

$$W_2 = \frac{1}{R612 \cdot C622}, \text{ and}$$

$$W_3 = \frac{1}{R613 \cdot C623}.$$

The solution to the transfer function given above for the point at which monitor 50 is connected to link 15 may be computed by sensing the particular electrical characteristics of link 15 at that point for the range of frequencies that is of interest. The electronics of equalizer 304 may then be adjusted and set accordingly. Alternatively, the transfer function may be solved off-line by making use of line records of the entity that designed and/or installed link 15, which records indicate the length, gauge and bridge-tap makeup of link 15. With this information and a mathematical simulation of the conventional telegrapher's equation, the impedance of link 15 at the point of interest may be determined. The numerator and the denominator coefficients of the equation may then be determined using this impedance. This will generally require the use of a transmission pole-and-zero-placing program in addition to the telegrapher's equation calculation. The pole-and-zero placer choses values for the poles and zeros which closely approximate the impedance of link 15 as specified by the equation. The coefficients of the equation are functions of the placed poles and zeros. The resulting equation for the impedance derived from line records closely matches the true impedance of the physical link. From this resulting equation, equalizer circuit 304 is derived, and it provides a close match to the impedance of the link. This close match is used as previously described to operate on the link current, to produce a voltage output from the equalizer 304 which is then used to separate oppositely-directed quats, as described below.

Equalizer 304 treats each band of frequencies as necessary in order to produce the maximum possible channel separation given the range and freedom of the equalizer. Illustratively, the amount of separation may be determined and minimized by the use of a simple multiplicative cross-correlator, placed at the outputs of circuits 305 and 306, which determines how much of each separated quat channel remains in the other. Error signals from the correlator drive the settings of the equalizer to a minimum correlation between the channels, which corresponds to the optimum quat channel separation.

The output of differential voltage probe interface 302, which is the sum of V1 and V2, and the output of equalizer 304, which is the difference of V1 and V2, serve as inputs to a sum circuit 305 and a difference circuit 306. Both circuits 305 and 306 are conventional; illustratively, they comprise wideband op-amps. Circuit 305 generates the sum of the two inputs, which is 2V1. Circuit 306 generates the difference of the two inputs, which is 2V2. These sum and difference signals are then respectively conducted to decoder 52 by leads 53 and 54.

Figure 7:
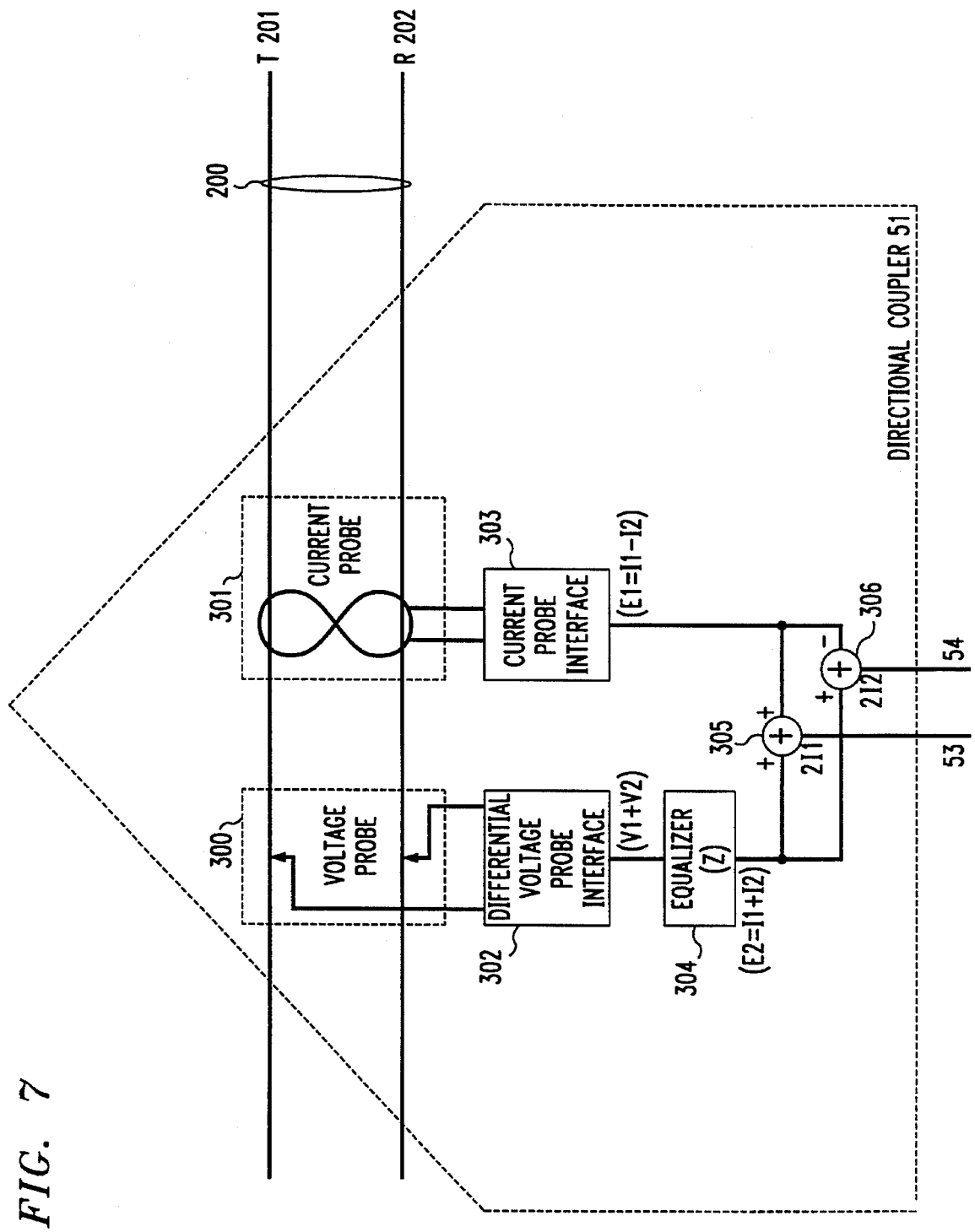
FIG. 7 is a block diagram of a second illustrative implementation of the bridging device of the monitor of the system of FIG. 1.

Of course, it should be understood that various changes and modifications to the illustrative embodiment described above will be apparent to those skilled in the art. For example, the directional coupler need not be bidirectional in all applications, but may detect and/or couple to the protocol analyzer only signals representative of only one direction of transmission on the monitored link. Furthermore, the signal-processing performed by the directional coupler may be current-based instead of being voltage-based: the output of the voltage probe interface instead of the current probe interface may be applied to an equalizer, the equalizer may convert the output of the voltage probe interface to a representation of a current, and the summing circuit and the difference circuit may combine this representation of current with the representation of current that is output by the current probe interface to generate the requisite output signals, as shown in FIG. 7. Also, this invention may be used in other environments, for example, with conventional analog communication loops where it may be necessary to separate the two ends of a voice communication. Such changes and modifications can be made without departing from the spirit and the scope of the invention and without diminishing its attendant advantages. It is therefore intended that all such changes and modifications be covered by the following claims.

I claim:

1. An arrangement for monitoring a digital transmission link, comprising:

a directional coupler for non-invasively coupling in parallel to said digital transmission link, wherein said digital transmission link has digital pulses travelling in one direction on said digital transmission link and further has other digital pulses travelling in another direction on said digital transmission link, having a first output for putting out signals representing said digital pulses travelling in the one direction on said digital transmission link at said directional coupler; and a protocol analyzer connected to said first output of said directional coupler, for interpreting said signals representing said digital pulses travelling in the one direction on said digital transmission link, to determine the meaning of said digital pulses travelling in the one direction on said digital transmission link in a digital communications protocol used on said digital transmission link.

2. The arrangement of claim 1 wherein said digital transmission link is a full-duplex digital transmission link, wherein:

the directional coupler is a bidirectional coupler non-invasively coupled in parallel to the link and having the first output, and a second output for putting out signals representing said digital pulses travelling in the other direction on the link at the directional coupler; and the protocol analyzer is connected to the first and to the second outputs and interprets the signals on each output to determine the meaning in the protocol of the digital pulses travelling on the link in each direction.

3. The arrangement of claim 1 wherein the directional coupler comprises:

a voltage sensor for measuring voltage on the link;

a current sensor for measuring current on the link; and means coupled to the voltage sensor and the current sensor for generating the signals representing the digital pulses from the measured voltage and current.

4. The arrangement of claim 1 wherein the directional coupler comprises:

means for measuring a sum of voltages of signals on a plurality of conductors of the link;

means for measuring a difference of currents of signals on the plurality of conductors of the link;

means for either converting the measured said difference of currents into a corresponding volume measurement or converting the measured said sum of voltages into a corresponding current measurement; and means for generating at the first output signals representing one of a sum and a difference of the said sum of voltages or said difference of current, respectively, and the converted measurement.

5. The arrangement of claim 4 wherein:

the means for measuring a sum comprise a voltage probe having two leads each in conductive contact with a different one of a pair of conductors of the link for sensing the voltages of signals on the conductors, and a differential voltage probe interface coupled to the voltage probe for generating a first signal representing the sum between the sensed signal voltages; and the means for measuring a difference comprise a current probe not in conductive contact with, and electromagnetically coupled to, the pair of conductors for sensing the currents of signals on the conductors, and a current probe interface coupled to the current probe for generating a second signal representing the difference of the sensed signal currents.

6. The arrangement of claim 5 wherein the converting means comprise:

an equalizer connected to the current probe interface for converting the second signal into a third signal representing the difference of the signal voltages on the pair of conductors.

7. The arrangement of claim 6 wherein the generating means comprise:

one of a sum circuit and a difference circuit for combining the first signal with the third signal and generating at the first output a signal representing the combination.

8. The arrangement of claim 1 wherein:

the transmission link is a subscriber loop having a tip conductor and a ring conductor;

the digital communications protocol is ISDN; and the represented digital pulses are quats.

9. An arrangement for monitoring a full-duplex transmission link having two conductors, comprising:

means for measuring a sum of voltages of signals on said two conductors;

means for measuring a difference of currents of signals on said two conductors;

means coupled to one of the measuring means for either converting the measured said difference of currents into a corresponding voltage measurement or converting the measured said sum of voltages into a corresponding current measurement;

means coupled to the other of the measuring means and to the converting means for generating a first signal indicative of a sum of the and said sum of voltages or said different of currents, respectively, the convened measurement, the first signal representing a signal travelling on the transmission link in one direction; and means coupled to the other of the measuring means and to the converting means for generating a second signal indicative of a difference of the said sum of voltages or said difference of current, respectively, and the corresponding measurement of the convened measurement, the second signal representing a signal travelling on the transmission link in the other direction.

10. The arrangement of claim 9 further comprising:

means coupled to at least one of the generating means for processing the first or the second signal generated by the at least one generating means to interpret a meaning of the signal travelling on the transmission link in at least a first direction.

11. The arrangement of claim 9 wherein:

the transmission link is a digital transmission link, and the first and the second signals represent digital pulses travelling on the link in only the one and in only the other direction, respectively.

12. The arrangement of claim 11 wherein:

the digital transmission link is a digital ISDN-protocol subscriber loop having a tip conductor and a ring conductor, and the digital pulses are quats.

13. The arrangement of claim 9 wherein:

the means for measuring a sum comprise a voltage sensor for non-invasively measuring the sum of signal voltages on the two conductors; and the means for measuring a difference comprise a current sensor for non-invasively measuring the difference of signal currents on the two conductors.

14. The arrangement of claim 9 wherein:

the means for measuring a sum comprise a voltage probe having two leads each in conductive contact with a different one of the two conductors for sensing the signal voltages on the conductors, and a differential voltage probe interface coupled to the voltage probe for generating a third signal representing the sum of the sensed signal voltages; and the means for measuring a difference comprise a current probe not in conductive contact with and electromagnetically coupled to the two conductors for sensing the signal currents on the conductors, and a current probe interface coupled to the current probe for generating a fourth signal representing the difference of the sensed signal currents.

15. The arrangement of claim 14 wherein the converting means comprise:

an equalizer connected to the current probe interface for converting the fourth signal into a fifth signal representing the difference of the signal voltages on the two conductors.

16. The arrangement of claim 15 wherein:

the means for generating the first signal comprise a sum circuit for additively combining the third signal with the fifth signal into the first signal; and the means for generating the second signal comprise a difference circuit for subtratively combining the third signal with the fifth signal into the second signal.

17. The arrangement of claim 14 wherein:

the two conductors conduct current in opposite directions;

the current probe includes a magnetic core defining an opening for threading the two conductors therethrough; and both conductors are threaded through the opening in the core and one of the two conductors is threaded backwards through the opening, such that the two conductors conduct current in the same direction through the opening.

18. A method of monitoring a digital transmission link that has digital pulses travelling in one direction on said digital transmission link and further has other digital pulses travelling in another direction on said digital transmission link, comprising the steps of:

non-invasively coupling a directional coupler in parallel to said digital transmission link;

generating signals at the coupler representing said digital pulses travelling in the one direction on said digital transmission link at said directional coupler; and interpreting the generated signals via a protocol analyzer to determine the meaning of said digital pulses travelling in the one direction on said digital transmission link in a digital communications protocol used on said digital transmission link.

19. The method of claim 18 for monitoring the digital transmission link that is a full-duplex digital transmission link, wherein:

the step of coupling comprises the step of non-invasively coupling a bidirectional coupler in parallel to the link;

the step of generating comprises the steps of generating first signals at the coupler representing the digital pulses travelling in the one direction on the link at the directional coupler, and generating second signals at the coupler representing said digital pulses travelling in the other direction on the link at the directional coupler; and the step of interpreting comprises the step of interpreting both the generated first and second signals via a protocol analyzer to determine the meaning in the protocol of the pulses travelling on the link in each direction.

20. The method of claim 18 wherein
the step of coupling comprises the steps of:
non-invasively coupling a voltage sensor to the link;
non-invasively coupling a current sensor to the link;
measuring voltage on the link with the voltage sensor;
measuring current in the link with the current sensor; and
generating the signals representing the digital pulses from the measured voltage and current.

21. The method of claim 18 wherein
the step of generating comprises the steps of:
measuring a sum of voltages of signals on a plurality of conductors of the link;
measuring a difference of currents of signals on the plurality of conductors of the link;
converting either the measured said difference of currents into a corresponding voltage measurement or converting the measured said sum of voltages into a corresponding current measurement; and
generating signals representing one of a sum and a difference of the said sum of voltages or said difference of currents, respectively, and the convened measurement.

22. The method of claim 21 wherein:
the step of coupling comprises the steps of
placing two leads of a voltage probe in conductive contact each with a different one of two conductors of the link, and
electromagnetically coupling a current probe, that is not in conductive contact with the two conductors, to the two conductors;
the step of measuring a sum comprises the steps of
sensing the signal voltages on the conductors with the voltage probe, and
generating a third signal representing the sum of the sensed signal voltages; and
the step of measuring a difference comprises the steps of
sensing the signal currents on the conductors with the current probe, and
generating a fourth signal representing the difference of the sensed signal currents.

23. The method of claim 22 wherein
the step of converting comprises the step of:
using an equalizer to convert the second signal into a third signal representing the difference of the Signal voltages on the two conductors.

24. The method of claim 23 wherein the step of generating comprises the steps of:
combining the first signal with the third signal, and
generating at the first output a signal representing the combination.

25. A method of monitoring a full-duplex transmission link having two conductors, comprising the steps of:
measuring a sum of voltages of signals on said two conductors;
measuring a difference of currents of signals on said two conductors;
converting either the measured said difference of currents into a corresponding voltage measurement or the measured said sum of voltages into a corresponding current measurement;
generating a first signal indicative of a sum of the said sum of voltages or said difference of currents, respectively, and the converted measurement, the first signal representing a signal travelling on the transmission link in one direction; and
generating a second signal indicative of a difference of the said sum of voltages or said difference of currents, respectively, and the converted measurement, the second signal representing a signal travelling on the transmission link in the other direction.

26. The method of claim 25 comprising the further step of:
processing at least one of the first or the second signal to interpret a meaning of the signal travelling on the transmission link in at least a first direction.

27. The method of claim 25 wherein:
the transmission link is a digital transmission link, and
the first and the second signals represent digital pulses travelling on the link in only the one and in only the other direction, respectively.

28. The method of claim 27 wherein:
the digital transmission link is a digital ISDN-protocol subscriber loop having a tip conductor and a ring conductor, and
the digital pulses are quats.

29. The method of claim 25 wherein:
the step of measuring a sum comprises the step of
using a voltage sensor to non-invasively measure the sum of signal voltages on the two conductors; and
the step of measuring a difference comprises the step of
using a current sensor to non-invasively measure the difference of signal currents on the two conductors.

30. The method of claim 25 wherein:
the step of measuring a sum comprises the step of
placing two leads of a voltage probe in conductive contact each with a different one of the two conductors to sense the signal voltages on the conductors, and
generating a third signal representing the sum of the sensed signal voltages; and
the step of measuring a difference comprises the step of
electromagnetically coupling a current probe, that is not in conductive contact with the two conductors, to the two conductors to sense the signal currents on the conductors, and
generating a fourth signal representing the difference of the sensed signal currents.

31. The method of claim 30 wherein
the step of converting comprises the step of:
using an equalizer to convert the fourth signal into a fifth signal representing the difference of the signal voltages on the two conductors.

32. The method of claim 31 wherein:
the step of generating the first signal comprises the step of
additively combining the third signal with the fifth signal into the first signal; and
the step of generating the second signal comprises the step of
subtractively combining the third signal with the fifth signal into the second signal.

33. The method of claim 25 wherein:
the step of electromagnetically coupling comprises the step of
threading both conductors, each conducting current in an opposite direction, through an opening defined by a magnetic core included in the current probe, but threading one of the two conductors backwards through the opening such that the two conductors conduct current in the same direction through the opening.

* * * * *